United States Patent [19]

Corless et al.

[11] Patent Number: 5,470,884
[45] Date of Patent: Nov. 28, 1995

[54] ANTI-ACNE COMPOSITIONS

[75] Inventors: Ann M. Corless, Fairfield; George E. Deckner, Cincinnati; Bonnie J. Hall, Mason; Joseph A. Listro, Loveland, all of Ohio

[73] Assignee: Procter & Gamble, Cincinnati, Ohio

[21] Appl. No.: 245,777

[22] Filed: May 19, 1994

[51] Int. Cl.$^6$ ................................................ A61K 31/075
[52] U.S. Cl. ........................................... 514/714; 514/864
[58] Field of Search ..................................... 514/714, 864

[56] References Cited

U.S. PATENT DOCUMENTS

| | | | |
|---|---|---|---|
| 2,798,053 | 7/1957 | Brown | 260/2.2 |
| 3,535,422 | 10/1970 | Cox et al. | 424/164 |
| 4,122,029 | 10/1978 | Gee et al. | 252/309 |
| 4,265,878 | 5/1981 | Keil | 424/68 |
| 4,387,107 | 6/1983 | Klein et al. | 424/338 |
| 4,401,835 | 8/1983 | Tarasov | 568/559 |
| 4,421,769 | 12/1983 | Dixon et al. | 424/358 |
| 4,509,949 | 4/1985 | Huang et al. | 546/558 |
| 4,593,046 | 6/1986 | Gruber | 514/717 |
| 4,599,379 | 7/1986 | Flesher et al. | 524/801 |
| 4,608,392 | 8/1986 | Jacquet et al. | 514/844 |
| 4,609,674 | 9/1986 | Gupte | 514/547 |
| 4,628,078 | 12/1986 | Glover et al. | 526/303.1 |
| 4,671,956 | 6/1987 | Bouillon et al. | 424/59 |
| 4,678,663 | 7/1987 | Scott et al. | 424/62 |
| 4,692,329 | 9/1987 | Klein et al. | 424/81 |
| 4,720,353 | 1/1988 | Bell | 252/309 |
| 4,725,429 | 2/1988 | Scott et al. | 424/62 |
| 4,835,206 | 5/1989 | Farrar et al. | 524/457 |
| 4,849,484 | 7/1989 | Heard | 525/221 |
| 4,857,302 | 8/1989 | Decker, Jr. et al. | 424/47 |
| 4,925,666 | 5/1990 | Decker, Jr. et al. | 424/78 |
| 5,086,075 | 2/1992 | De Villez | 514/714 |
| 5,100,660 | 3/1992 | Hawe et al. | 424/78 |

FOREIGN PATENT DOCUMENTS 0288868  12/1986  European Pat. Off. .

*Primary Examiner*—Richard L. Raymond
*Attorney, Agent, or Firm*—Anthony D. Sabatelli; Leonard W. Lewis; David L. Suter

[57] ABSTRACT

The present invention relates to anti-acne compositions having good efficacy, low skin irritation, and good physical and chemical stability. These compositions comprise a benzoyl peroxide, a wetting agent, water, a non-volatile emollient component which is a liquid at 25° C. and which has a weighted arithmetic mean solubility parameter of less than or equal to about 7, and a water soluble or dispersible gelling agent.

20 Claims, No Drawings

ANTI-ACNE COMPOSITIONS

TECHNICAL FIELD

The present invention relates to topical anti-acne compositions containing benzoyl peroxide. These compositions are effective for the treatment of acne and also have low skin irritation and good chemical and physical stability. In further embodiments, the present invention also relates to methods for the treatment of acne.

BACKGROUND OF THE INVENTION

Acne is a common inflammatory pilosebaceous disease characterized by comedones, papules, pustules, inflamed nodules, and pus-filled cysts. The pathogenesis of acne is complex and is believed to involve an interaction between hormones, keratinization, sebum, and bacteria. Acne usually begins at puberty when the increase of androgens causes an increase in the size and activity of the sebum producing ducts. These ducts can subsequently become blocked, leading to hyperkeratinization and the formation of acne lesions.

Many topical therapeutic agents are employed in the treatment of acne. It is believed that these anti-acne agents work by preventing the blockage of the ducts, by reopening clogged ducts, by acting against infecting bacteria, and by providing a keratolytic effect. Compositions containing benzoyl peroxide are known to be effective for the treatment of acne. For example, U.S. Pat. No. 3,535,422, to Cox et al., issued Oct. 20, 1970 discloses compositions containing dispersed benzoyl peroxide in a fluid medium containing water and an organic emollient; U.S. Pat. No. 4,609,674, to Gupte, issued Sep. 2, 1986, discloses stable anhydrous compositions containing benzoyl peroxide in a $C_6$ to $C_{10}$ triglyceride; U.S. Pat. No. 4,720,353 to Bell, issued Jan. 19, 1988 discloses water-in-oil emulsion compositions containing benzoyl peroxide; and U.S. Pat. No. 4,387,107, to Klein et al., issued Jun. 7, 1983 discloses aqueous benzoyl peroxide compositions employing dioctyl sodium sulfosuccinate as a wetting agent.

Even though the use of benzoyl peroxide for the treatment of acne is well known, benzoyl peroxide has the disadvantage of being very irritating to the skin, causing symptoms such as excessive drying, scaling, swelling, burning, peeling, redness, allergic contact dermatitis, and sensitization. This irritation problem associated with benzoyl peroxide can cause a patient to discontinue or to reduce its usage, thereby sacrificing the anti-acne benefit. See, e.g., Brogden et al., *Drugs* 8, 417 (1974); Poole et al., *Arch. Derm.* 102, 400 (1972); Eaglstein, *Arch. Derm.*, 97,527 (1968); Pace, *Can. Med. Ass. J.*, 93, 252 (1965); Vasarinsh, *Arch. Derm.*, 98, 183 (1968); Mysliborski et al., AFP 15, 86 (1977) Hare, *Br. J. Clin. Prac;*, 29, 63 (1975); Fulton, et al., *Arch. Derm.*, 110, 83 (1974); and Wilkinson, et al., *Can. Med Assn. J.*, 95, 28 (1966).

Many conventional benzoyl peroxide compositions also have poor physical and chemical stability, and tend to lose their anti-acne effectiveness and aesthetic qualities over relatively short periods of time.

The compositions of the present invention have good anti-acne efficacy, have low skin irritancy, and are physically and chemically stable. These compositions comprise a dispersion of benzoyl peroxide in a thickened vehicle containing water and a nonvolatile liquid emollient component wherein the weighted arithmetic mean solubility parameter of the constituents of the emollient is less than or equal to about 7. Without being limited by theory, it is believed that in selecting an emollient component with this solubility parameter requirement that the solubilization of the benzoyl peroxide into the product vehicle is minimized, thereby reducing the incidence of unwanted skin irritation and other undesired side effects due to excessive epidermal penetration. It is also believed that the emollient component provides the additional benefit of coating and soothing the skin, thereby further mitigating any potentially irritating effects from the benzoyl peroxide. Also, it is believed that the limited solubility of the benzoyl peroxide in the present compositions provides enhanced chemical and physical stability of the compositions.

It is therefore an object of the present invention to provide topical compositions for the treatment of acne.

It is another object of the present invention to provide topical compositions for the treatment of acne, which comprise benzoyl peroxide as the active ingredient, and which have good efficacy, low skin irritation, and good physical and chemical stability.

It is another object of the present invention to provide a method for treating acne in human skin.

These and other objects of this invention will become apparent in light of the following disclosure.

SUMMARY OF THE INVENTION

The present invention relates to an anti-ache composition comprising:

(a) from about 0.1% to about 20% benzoyl peroxide, (b) from about 0.01% to about 10% of a wetting agent, (c) from about 20% to about 99.74% water, (d) from about 0.1% to about 10% of a non-volatile emollient component which is a liquid at 25° C. and which has a weighted arithmetic mean solubility parameter of less than or equal to about 7, and (e) from about 0.05% to about 5% of a water soluble or dispersible gelling agent.

All percentages and ratios used herein are by weight of the total composition and all measurements made are at 25° C., unless otherwise designated. All weight percentages, unless otherwise indicated, are on an actives weight basis. The invention hereof can comprise, consist of, or consist essentially of, the essential as well as optional ingredients and components described herein.

DETAILED DESCRIPTION OF THE INVENTION

The compositions of the present invention are useful for treating acne in human skin, i.e. for providing an anti-acne benefit.

The term "chemical stability", as used herein, means that the compositions of the present invention do not exhibit an appreciable breakdown, degradation, disappearance, reaction, or consumption of the benzoyl peroxide. For example, the compositions of the present invention typically retain at least about 80% of the initially added benzoyl peroxide over a period of about 3 months at 45° C.

The term "physical stability", as used herein, means that the compositions of the present invention exhibit physical characteristics such as pH stability, resistance to loss of viscosity, resistance to discoloration, resistance to developing off-odors, and the like. For example, the compositions of the present invention typically maintain their physical stability for at least about 3 months at 45° C.

The terms "chemical stability" and "physical stability" have been separately defined herein for convenience. Nevertheless, it is realized that these two types of stability phenomena are not necessarily distinct and that chemical stability can impact physical stability and vice versa.

The term "topical application", as used herein, means to apply or spread the anti-acne compositions to the surface of the skin.

The term "pharmaceutically-acceptable", as used herein, means that the compositions or components thereof so described are suitable for use in contact with human tissue without undue toxicity, incompatibility, instability, allergic response, and the like.

Benzoyl Peroxide

The compositions of the present invention comprise from about 0.1% to about 20%, more preferably from about 0.5% to about 15%, and most preferably from about 2.5% to about 10% of benzoyl peroxide.

Benzoyl peroxide, which is also known as dibenzoyl peroxide, can be represented by the chemical formula $C_{14}H_{10}O_4$ and the following chemical structure.

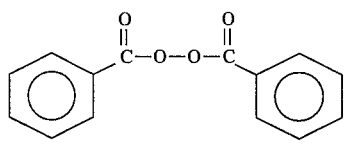

See *The Merck Index*, Tenth Edition, entry 1119, p. 159 (1983), which is incorporated by reference herein in its entirety.

In the compositions of the present invention, the benzoyl peroxide particles are not limited to any particular size and can span a broad range of particle sizes. However, it is found that benzoyl peroxide particles having an average particle size diameter from about 0.5 microns to about 40 microns are preferred. More preferred are those having an average particle size diameter from about 1 micron to about 20 microns. Most preferred are those having an average particle size diameter from about 1 micron to about 10 microns.

Wetting Agent

The compositions of the present invention comprise from about 0.01% to about 10%, more preferably from about 0.01% to about 5%, and most preferably from about 0.01% to about 1% of a wetting agent. The wetting agent can be a single chemical compound as well as mixtures of two or more chemical compounds.

Without being limited by theory it is believed that the wetting agent coats the surface of the benzoyl peroxide particles and lowers their surface tension, thereby helping to maintain the benzoyl peroxide as a dispersion in the formulation matrix and aiding the distribution of the benzoyl peroxide upon the skin.

A wide variety of wetting agents useful in the present invention are disclosed in McCutcheon's Volume 2: Functional Materials, North American Edition pp. 117–137 (1992) and CTFA Cosmetic Ingredient Handbook, Second Edition, p. 597 (Section Entitled Suspending Agents) (1992), both of which are incorporated by reference herein in their entirety.

A preferred wetting agent is a dimethicone copolyol, which is a polymer of dimethylsiloxane with polyoxyethylene and/or polyoxypropylene side chains. A typical dimethicone copolyol is represented by the chemical formula $(CH_3)_3SiO[(CH_3)_2SiO]_x[(CH_3)RSiO]_ySi(CH_3)_3$ wherein R is $C_3H_5O(C_2H_4O)_m(C_3H_6O)_nH$, x is an integer from about 1 to about 500, y is an integer from about 1 to about 500, m is an integer from about 1 to about 250, and n is an integer from about 1 to about 250, (these integer values being chosen to achieve the desired molecular weight and degree of ethoxylation and propoxylation). Examples of commercially available dimethicone copolyols useful herein are sold by Dow Corning Corporation as Dow Corning® 190, 193, Q2-5220, 2501 Wax, 2--5324 fluid, and 3225C (this later material being sold as a mixture with cyclomethicone). Preferred among these materials are the Dow Corning® 190 and 193 silicone copolyol materials. See DiSapio et al., "Silicone Glycols For Cosmetic And Toiletry Application", IFSCC, September 1988, London; Dow Corning Technical Bulletin, Shaping Solutions For Personal Care", 1993; U.S. Pat. No. 4,122,029, to Gee et al., issued Oct. 24, 1978, U.S. Pat. No. 4,265,878, to Keil, issued May 5, 1981; and U.S. Pat. No. 4,421,769, to Dixon et al., issued Dec. 20, 1983, all of which are incorporated by reference herein in their entirety.

Nonlimiting examples of other wetting agents include the following materials dioctyl sodium sulfosuccinate, sodium lauraminodipropionate, caprylyl pyrollidone, dimethyl octynediol, tetramethyl decynediol, and mxitures thereof. Preferred among these other wetting agents is dioctyl sodium sulfosuccinate, which is described in the *CTFA Cosmetic Ingredient Handbook* Second Edition 1992, p. 127, which is incorporated by reference herein in its entirety.

Also, useful as wetting agents in the present invention are various fluorinated and perfluorined materials such as the Fluorad™ fluorochemical surfactants described in The 3M Company's Product Information Bulletin Entitled *Flourad Fluorochemical Surfactants*, March 1993, which is incorporated by reference herein in its entirety. A preferred fluorinated wetting agent among these materials is a fluorinated alkyl ester sold under the tradename FC-430.

Water

The compositions of the present invention comprise from about 20% to about 99.74%, more preferably from about 50% to about 95%, and most preferably from about 70% to about 90% of water.

Non-volatile Emollient Component

The compositions of the present invention comprise from about 0.1% to about 10%, more preferably from about 0.5% to about 7.5%, and most preferably from about 1% to about 5% of a non-volatile emollient component that is a liquid at about 25° C. and that has a weighted arithmetic mean solubility parameter of less than or equal to about 7. By "emollient" component is meant that the material is soothing to the skin or mucous membranes and is effective in making the skin feel soft, smooth, or supple. By "liquid at about 25° C." is meant that the emollient component has a melting point, at 1 atmosphere pressure, that is less than or equal to about 25° C. By "nonvolatile" is meant that the emollient component has a boiling point, at 1 atmosphere pressure, greater than or equal to about 100° C. The emollient components useful herein can include a single chemical compound as well as mixtures of two or more chemical compounds as long as the overall emollient component meets the melting point, boiling point, and solubility parameter requirements described herein.

The emollients useful herein preferably have a weighted arithmetic mean solubility parameter of less than or equal to about 7, preferably from about 1 to about 6.5, more preferably from about 5 to about 6.5, and most preferably from about 5 to about 6. Solubility parameters are well known to the formulation chemist of ordinary skill in the art and are routinely used as a guide for determining compatibilities and solubilities of materials in the formulation process. Without being limited by theory, it is believed that by choosing a nonvolatile, liquid emollient component having a low solubility parameter, that the solubility of the relatively polar benzoyl peroxide molecule in the emollient component will be minimized, thereby diminishing undue skin irritation caused by excessive epidermal penetration of the benzoyl peroxide. Also, it is believed that the nonvolatile, liquid emollients provide the additional benefit of coating and soothing the skin, thereby protecting against irritation by the benzoyl peroxide.

The solubility parameter of a chemical compound, $\delta$, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\sum_i E_i$=the sum of the heat of vaporization additive group contributions, and $\sum_i m_i$=the sum of the molar volume additive group contributions Standard tabulations of heat of vaporization and molar volume additive group contributions for a wide variety of atoms and groups of atoms are collected in Barton, A. F. M. *Handbook of Solubility Parameters*, CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", *Polymer Engineering and Science*, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, *Handbook of Chemistry and Physics*, 57th edition, CRC Press, p. C-726 (1976–1977), which is incorporated by reference herein in its entirety.

Formulation chemists typically report and use solubility parameters in units of $(cal/cm^3)^{1/2}$. The tabulated values of additive group contributions for heat of vaporization in the *Handbook of Solubility Parameters* are reported in units of kJ/mol. However, these tabulated heat of vaporization values are readily converted to cal/mol using the following well-known relationships:

1J/mol=0.239006cal/mol and 1000J=1kJ.

See Gordon, A. J. et al., *The Chemist's Companion*, John Wiley & Sons, pp. 456–463, (1972), which is incorporated by reference herein in its entirety.

Solubility parameters have also been tabulated for a wide variety of chemical materials. Tabulations of solubility parameters are found in the above-cited *Handbook of Solubility Parameters*.

A wide variety of nonvolatile emollients are useful herein, nonlimiting examples of which are listed in *McCutcheon's*, Vol. 2 *Functional Materials*, North American Edition, (1992), pp. 137–168, which is incorporated herein by reference in its entirety, and *CTFA Cosmetic Ingredient Handbook*, Second Edition (1992) which lists Skin-Conditioning Agents at pp. 572–575 and Skin Protectants at p. 580, which is also incorporated herein by reference in its entirety.

Among the nonvolatile emollient materials useful herein especially preferred are silicones, hydrocarbons, esters, and mixtures thereof.

Examples of silicone emollients include polyalkylsiloxanes, cyclic polyalkylsiloxanes, and polyalkylarylsiloxanes. The polyalkylsiloxanes useful herein include, for example, polyalkylsiloxanes with viscosities of from about 0.5 to about 100,000 centistokes at 25° C. Such polyalkylsiloxanes correspond to the general chemical formula $R_3SiO[R_2SiO]_xSiR_3$ wherein R is an alkyl group (preferably R is methyl or ethyl, more preferably methyl) and x is an integer from 0 to about 500, chosen to achieve the desired molecular weight. Commercially available polyalkylsiloxanes include the polydimethylsiloxanes, which are also known as dimethicones, nonlimiting examples of which include the s Vicasil® series sold by General Electric Company and the Dow Corning® 200 series sold by Dow Corning Corporation. Specific examples of polydimethylsiloxanes useful as emollients herein include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Cyclic polyalkylsiloxanes useful herein include those corresponding to the general chemical formula $[SiR_2O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6). Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids). Also useful Herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Hydrocarbons useful herein include straight and branched chain hydrocarbons having from about 10 to about 30 carbon atoms, more preferably from about 12 to about 24 carbon atoms, and most preferably from about 16 to about 22 carbon atoms. Nonlimiting examples of these hydrocarbon materials include dodecane, squalane, cholesterol, 5 hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Other hydrocarbon materials useful herein include paraffins and mineral oils such as USP light mineral oil (e.g., Klearol® available from Witco Corp., Melrose Park, Ill.) and USP heavy mineral oil (e.g. Klearol® available from Witco Corp., Melrose Park, Ill.).

Also useful as nonvolatile emollients are esters, including esters of monofunctional and difunctional fatty acids that have been esterified with alcohols and polyols (i.e. alcohols having two or more hydroxy groups). A wide variety of esters are useful herein, with long chain esters of long chain fatty acids being preferred (i.e. C10–40 fatty acids esterified with C10–40 fatty alcohols). Nonlimiting examples of esters useful herein include those selected from the group consisting of diisopropyl adipate, isopropyl myristate, isopropyl palmitate, myristyl propionate, ethylene glycol distearate, 2-ethylhexyl palmitate, isodecyl neopentanoate, $C_{12-15}$ alcohols benzoate, di-2-ethylhexyl maleate, cetyl palmitate, myristyl myristate, stearyl stearate, cetyl stearate, behenyl behenrate, and mixtures thereof.

Water Soluble or Dispersible Gelling Agent

The compositions of the present invention comprise from about 0.05% to about 5%, more preferably from about 0.1% to about 2.5%, and most preferably from about 0.25% to about 1% of a water soluble or dispersible gelling agent. By "water soluble or dispersible" as used herein means that the gelling agents are soluble or dispersible in water at a level of at least about 0.25% by weight at 25° C. The gelling agent can be a single chemical compound as well as mixtures of two or more chemical compounds.

Nonlimiting classes of water soluble or dispersible gelling agents include those selected from the group consisting of carboxylic acid polymers, crosslinked polyacrylate polymers, polyacrylamide polymers, polysaccharides, gums, vinyl ether/maleic anhydride copolymers, crosslinked poly(N-vinylpyrrolidones), and mixtures thereof. See U.S. Pat. No. , 4,387,107, to Klein et al., issued Jun. 7, 1983 which lists a variety of thickening or gelling agents, and which is incorporated herein by reference in its entirety.

Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl —CN —COOH and mixtures thereof). The second type of polymer is a crosslinked copolymer having a first monomer selected from the group consisting of an acrylic acid monomer or derivative thereof (as just described in the previous sentence), a short chain alcohol (i.e. a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN,—COOH, and mixtures thereof), and mixtures thereof; and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred red. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein. See also, *CTFA International Cosmetic Ingredient Dictionary*, fourth edition, 1991, pp. 12 and 80; which are also incorporated herein by reference in their entirety.

Examples of commercially availble homopolymers of the first type useful herein include the carbomers, which are homopolymers of acrylic acid crosslinked with allyl ethers of sucrose or pentaerytritol. The carbomers are available as the Carbopol® 900 series from B. F. Goodrich. Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10-30 alkyl acrylate crosspolymers and are commerically available as Carbopol® 1342, Pemulen TR-1, and Pemulen TR-2, from B. F. Goodrich. In other words, examples of carboxylic acid polymer thickeners useful herein are those selected from the group consisting of carbomers, acrylates/C 10-C30 alkyl acrylate crosspolymers, and mixtures thereof.

Crosslinked Polyacrylate Polymers

The crosslinked polyacrylate polymers useful as thickeners include both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The crosslinked polyacrylate polymers are high molecular weight materials that can be characterized by the general formula: $(A)_l(B)_m(C)_n$ and comprise the monomer units $(A)_l$, $(B)_m$, and $(C)_n$, wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer that is polymerizable with (A) or (B), for example a monomer having a carbon-carbon double bond or other such polymerizable functional group, 1 is an integer of 0 or greater, m is an integer of 0 or greater, n is an integer of 0 or greater, but where either 1 or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1$–$C_8$, preferably $C_1$–$C_5$, more preferably $C_1$–$C_3$, and most preferably $C_1$–$C^2$. When quaternzied, the polymers are preferably quaternized with short chain alkyls i.e. $C_1$–$C_8$, preferably $C_1$–$C_8$, more preferably $C_1$–$C_3$, and most preferably $C_1$–$C_2$. The acid addition salts refer to polymers having protonated amino groups. Acid addition salts can be performed through the use of halogen (e.g. chloride), acetic, phosphoric, nitric, citric, or other acids.

These $(A)_l(B)_m(C)_n$ polymers also comprise a crosslinking agent, which is most typically material containing two or more unsaturated functional groups. The crosslinking agent is reacted with the monomer units of the polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects in water or other aqueous carriers of the compositions hereof. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide, is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to o about 20:80. Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure $(A)_l(B)_m(C)_n$ wherein I is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-1 trideceth-6) under the trademark Salcare® SC92 from Allied Colloids Ltd. (Norfolk, Virginia). This polymer has the proposed CTFA designation, "Polyquaternium 32 (and) Mineral Oil".

Other cationic polymers useful herein, are those not containing acrylamide or other (C) monomers, that is, n is zero. In these polymers the (A) and (B) monomer components are as described above. An especially preferred group of these non-acrylamide containing polymers is one in which I is also zero. In this instance the polymer is essentially a homopolymer of a dialkylaminoalkyl methacrlyate monomer or its quaternary ammonium or acid addition salt. These diaklylaminoalkyl methacrylate polymers preferably contain a crosslinking agent as described above.

A cationic polymer, which is essentially a homopolymer, useful herein is one conforming to the general structure $(A)_l(B)_m(C)_n$ wherein I is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-1 trideceth-6 as a dispersing aid, from Allied Colloids Ltd, (Norfolk, VA) under the trademark Salcare® SC95. This polymer has recently been given the CTFA designation "Polyquaternium 37 (and) Mineral Oil (and) PPG-1 Trideceth-6".

Polyacrylamide Polymers

Also useful herein are polyacrylamide polymers, especially non-ionic polyacrylamide polymers including substituted branched or unbranched polymers. These polymers can be formed from a variety of monomers including acrylamide and methacrylamide which are unsubstituted or subtituted with one or two alkyl groups (preferably $C_1$ to $C_5$). Preferred are acrylate amide and methacrylate amide monomers in which the amide nitrogen is unsubstituted, or substituted with one or two $C_1$ to $C_5$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the non-ionic polymer given the CTFA designation polyacrylamide and isoparaffin and laureth7, available under the Tradename Sepigel from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Polysaccharides

A wide variety of polysaccharides are useful herein. By "polysaccharides" are meant gelling agents containing a backbone of repeating sugar (i.e. carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a C10–C30 straight chain or branched chain alkyl group through an ether linkage. Typically these polymers are ethers of C 10–C30 straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-→3) linked glucose units with a (1-→6) linked glucose every three units, a commercially available example of which is Clearogel™CS11 from Michel Mercier Products Inc. (Mountainside, N.J.). Gums Other gelling agents useful herein include materials which are primarily derived from natural sources. Nonlimiting examples of these gelling agent gums include materials selected from the group consisting of acacia, agar, algin, alginic acid, ammonium alginate, amylopectin, bentonite, calcium alginate, calcium carrageenan, carnitine, carrageenan, corn starch, dextrin, gelatin, gellan gum, guar gum, guar lo hydroxypropyltrimonium chloride, hectorite, hyaluroinic acid, hydrated silica, hydroxypropyl chitosan, hydroxypropyl guar, karaya gum, kelp, locust bean gum, magnesium aluminum silicate, manesium silicate, magnesium trisilicate, montmorillonite, natto gum, potassium alginate, potassium carrageenan, propylene glycol alginate, sclerotium gum, sodium carboyxmethyl dextran, sodium carrageenan, sodium polyacrylate starch, sodium silicoaluminate, starch/acrylates/acrylamide copolymer, tragacanth gum, xanthan gum, and mixtures thereof.

Crosslinked Vinyl Ether/Maleic Anhydride Copolymers

Other gelling agents useful herein include crosslinked copolymers of alkyl vinyl ethers and maleic anhdride. In these copolymers the vinyl ethers are represented by the formula R—O—CH═CH$_2$ wherein R is a C$_1$–C6 alkyl group, preferably R is methyl. Preferred crosslinking agents are C4–C20 dienes, preferably C6 to C16 dienes, and most preferably C8 to C12 dienes. A particularly preferred copolymer is one formed from methyl vinyl ether and maleic anhydride wherein the copolymer has been crosslinked with decadiene, and wherein the polymer when diluted as a 0.5% aqueous solution at pH 7 at 25° C. has a viscosity of 50,000–70,000 cps when measured using a Brookfield RTV viscometer, spindle #7 at 10 rpm. This copolymer has the CTFA designation PVM/MA decadiene crosspolymer and is commercially available as Stabileze™ 06 from International Specialty Products (Wayne N.J.).

Crosslinked poly(N-vinylpyrrolidones)

Crosslinked polyvinyl(N-pyrrolidones) useful herein as gelling agents include those described in U.S. Pat. No. 5,139,770, to Shih et al, issued Aug. 18, 1992, and U.S. Pat. No. 5,073,614, to Shih et al., issued Dec. 17, 1991, both patents of which are incorporated by reference herein in their entirety. These gelling agents typically contain from about 0.25% to about 1% by weight of a crosslinking agent selected from the group consisting of divinyl ethers and diallyl ethers of terminal diols containing from about 2 to about 12 carbon atoms, divinyl ethers and diallyl ethers of polyethylene glycols containing from about 2 to about 600 units, dienes having from about 6 to about 20 carbon atoms, divinyl benzene, vinyl and allyl ethers of pentaerythritol, and the like. Typically, these gelling agents have a viscosity from about 25,000 cps to about 40,000 cps when measured as a 5% aqueous solution at 25° C. using a Brookfield RVT viscometer with Spindle #6 at 10 rpm. Commercially available examples of these polymers include ACP-1120, ACP-1179, and ACP1180, available from International Specialty Products (Wayne, N.J.).

Additional Components

The compositions of the present invention can comprise a wide range of additional components. The CTFA *Cosmetic Ingredient Handbook*, Second Edition, 1992, which is incorporated by reference herein in its entirety, describes a wide variety of nonlimiting cosmetic and pharamceutical ingredients commonly used in the skin care industry, which are suitable for use in the compositions of the present invention. Nonlimiting examples of functional classes of ingredients are described at page 537 of this reference. Examples of these functional classes include: abrasives, absorbents, other anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, skin-conditioning agents (humectants, miscellaneous, and occulsive), sunscreen agents, and ultraviolet light absorbers.

Some nonlimiting examples of these additional components cited in the *CTFA Cosmetic Ingredient Handbook*, as well as other materials useful herein, include the following: vitamins and derivatives thereof (e.g tocopherol, tocopherol acetate, retinoic acid, retinol, retinoids, and the like); polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; other anti-acne medicaments (e.g., resorcinol, sulfur, salicylic acid, erythromycin, zinc, and the like); skin bleaching (or lightening) agents including but not limited to hydroquinone, kojic acid; antioxidants; chelators and sequestrants; and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabolol, dipotassium glycyrrhizinate and the like; and skin conditioning agents such as the propoxylated glycerols described in U.S. Pat. No. 4,976,953, to Orr et al., issued Dec. 11, 1990, which is incorporated by reference herein in its entirety.

Methods For Treating Acne

The compositions of the present invention are useful for treating acne in human skin. To obtain an anti-acne benefit, an effective amount of the compositions of the present invention are applied to the skin. The term "effective" means an amount of the compositions of the present invention to provide an anti-acne benefit, but not so much as to cause any undesirable side effects or skin reactions.

A wide range of quantities of the compositions of the present invention can be employed to provide an anti-acne benefit. Quantities of the present compositions which are typically applied to provide an anti-acne benefit can range from about 0.1 mg/cm$^2$ to about 10 mg/cm$^2$. A particularly useful amount to use is about 2 mg/cm$^2$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE 1

Anti-Acne Gel

An anti-acne gel is prepared by combining the following ingredients using conventional mixing techniques.

| Ingredients | Weight Percent |
| --- | --- |
| Water | qs100 |
| Benzoyl Peroxide[1] | 10.00 |
| Carbomer 980[2] | 0.65 |
| Disodium EDTA | 0.10 |
| Sodium Hydroxide | 0.12 |
| Dimethicone Copolyol[3] | 0.10 |
| Dimethicone[4] | 1.0 |

[1]Lucidol® 700 from Elf Atochem, which is a powder containing 70% benzoyl peroxide active. 14.29% percent of this powder is added to the composition to account for the 70% activity.
[2]Carbopol® 980 from B.F. Goodrich.
[3]Dow Corning® 193 from Dow Corning.
[4]Dow Corning® 200 Fluid (350 centistoke) from Dow Corning.

In a suitable vessel a benzoyl peroxide slurry is prepared by combining the benzoyl peroxide with approximately 17% of the water. This slurry is passed through a Colloid or Urschel mill to disperse the benzoyl peroxide, followed by rinsing the mill with approximately an additional 6% of the water, this rinse being added to the total slurry.

In a separate vessel a 5% sodium hydroxide solution is prepared using approximately 2.5% of the water.

In another vessel the carbomer 980 is gradually combined with the remaining water with agitation to disperse and hydrate the carbomer. The carbomer dispersion is then transferred to a vessel equipped with a high shear mixer (Day Mixer, Serial No. 88612, Day Mixing, Cincinnati, Ohio.) for blending the remaining ingredients. Next, the disodium EDTA is added and mixed until dissolved. The dimethicone copolyol is then added and stirred until uniform. Next, the benzoyl peroxide slurry is added and the mixture is stirred until uniform. The dimethicone is then added and the mixture stirred for 5 minutes to fully disperse the silicone. Next, the 5% NaOH solution is gradually added with continuous mixing. The compositions is then mixed for 3–5 minutes until homogeneous.

The resulting anti-acne composition exhibits low skin irritation and good physical and chemical stability, and is useful for topical application to human skin for the treatment of acne.

EXAMPLE 2

Anti-Acne Gel

An antiacne gel is prepared by combining the following ingredients using conventional mixing techniques.

| Ingredients | Weight Percent |
| --- | --- |
| Water | qs100 |
| Benzoyl Peroxide[1] | 10.00 |
| Carbomer 980[2] | 0.65 |
| Disodium EDTA | 0.10 |
| Sodium Hydroxide | 0.12 |
| Bentonite | 1.0 |
| Dimethicone Copolyol[3] | 0.10 |
| Dimethicone[4] | 1.0 |

[1]Lucidol ® 70 from Elf Atochem, which is a powder containing 70% benzoyl peroxide active. 14,29% percent of this powder is added to the composition to account for the 70% activity.
[2]Carbopol ® 980 from B.F. Goodrich.
[3]Dow Corning ® 193 from Dow Corning.
[4]Dow Corning ® 200 Fluid (350 centistokes) from Dow Corning.

In a suitable vessel a benzoyl peroxide slurry is prepared by combining the benzoyl peroxide with 17% of the water. This slurry is passed through a Colloid or Urschel mill to disperse the benzoyl peroxide, followed by rinsing the mill with approximately an additional 6% of the water, this rinse being added to the total slurry.

In a separate vessel a 5% sodium hydroxide solution is prepared using 2.5% of the water.

In another vessel the carbomer 980 is gradually combined with the remaining water with agitation to disperse and hydrate the carbomer. The carbomer dispersion is then transferred to a vessel equipped with a high shear mixer (Day Mixer, Serial No. 88612, Day Mixing, Cincinnati, Ohio.) for blending the remaining ingredients. Next, the disodium EDTA is added and mixed until dissolved. The dimethicone copolyol is then added and stirred until uniform. The bentonite is added to the mixture which is stirred with sufficient agitation until dispersed. Next, the benzoyl peroxide slurry is added and the mixture is stirred until uniform. The dimethicone is then added and the mixture stirred for 5 minutes to fully disperse the silicone. Next, the 5% NaOH solution is gradually added with continuous mixing. The compositions is then mixed for 3–5 minutes until homogeneous.

The resulting anti-acne composition exhibits low skin irritation and good physical and chemical stability, and is useful for topical application to human skin for the treatment of acne.

EXAMPLE 3

Anti-Acne Gel

An antiacne gel is prepared by combining the following ingredients using conventional mixing techniques.

| Ingredient | Weight Percent |
| --- | --- |
| Water | qs100 |
| Benzoyl Peroxide[1] | 2.50 |
| Carbomer 980[2] | 0.65 |
| Disodium EDTA | 0.10 |
| Sodium Hydroxide | 0.12 |
| Bentonite | 1.0 |
| Dimethicone Copolyol[3] | 0.10 |
| Dimethicone[4] | 1.0 |

[1]Lucidol ® 70 from Elf Atochem, which is a powder containing 70% benzoyl peroxide active. 3.57% percent of this powder is added to the composition to account for the 70% activity.
[2]Carbopol ® 980 from B.F. Goodrich.
[3]Dow Corning ® 193 from Dow Corning.
[4]Dow Corning ® 200 Fluid (350 centistokes) from Dow Corning.

In a suitable vessel a benzoyl peroxide slurry is prepared by combining the benzoyl peroxide with 17% of the water. This slurry is passed through a Colloid or Urschel mill to disperse the benzoyl peroxide, followed by rinsing the mill with approximately an additional 6% of the water, this rinse being added to the total slurry.

In a separate vessel a 5% sodium hydroxide solution is prepared using 2.5% of the water.

In another vessel the carbomer 980 is gradually combined with the remaining water with agitation to disperse and hydrate the carbomer. The carbomer dispersion is then transferred to a vessel equipped with a high shear mixer (Day Mixer, Serial No. 88612, Day Mixing, Cincinnati, Ohio.) for blending the remaining ingredients. Next, the disodium EDTA is added and mixed until dissolved. The dimethicone copolyol is then added and stirred until uniform. The bentonite is added to the mixture which is stirred with sufficient agitation until dispersed. Next, the benzoyl peroxide slurry is added and the mixture is stirred until uniform. The dimethicone is then added and the mixture stirred for 5 minutes to fully disperse the silicone. Next, the 5% NaOH solution is gradually added with continuous mixing. The compositions is then mixed for 3–5 minutes until homogeneous.

The resulting anti-acne composition exhibits low skin irritation and good physical and chemical stability, and is useful for topical application to human skin for the treatment of acne.

EXAMPLE 4

Anti-Acne Gel

An antiacne gel is prepared by combining the following ingredients using conventional mixing techniques.

| Ingredients | Weight Percent |
| --- | --- |
| Water | qs100 |
| Benzoyl Perxodie[1] | 10.00 |
| Carbomer 980[2] | 0.65 |
| Disodium EDTA | 0.10 |
| Sodium Hydroxide | 0.12 |
| Bentonite | 1.0 |
| Dioctyl Sodium Sulfosuccinate | 0.10 |
| Dimethicone[3] | 1.0 |

[1]Lucidol ® 70 from Elf Atochem, which is a powder containing 70% benzoyl peroxide active. 14.29% percent of this powder is added to the composition to account for the 70% activity.
[2]Carbopol ® 980 from B.F. Goodrich.
[3]Dow Corning ® 200 Fluid (350 centistokes) from Dow Corning.

In a suitable vessel a benzoyl peroxide slurry is prepared by combining the benzoyl peroxide with 17% of the water. This slurry is passed through a Colloid or Urschel mill to disperse the benzoyl peroxide, followed by rinsing the mill with approximately an additional 6% of the water, this rinse being added to the total slurry.

In a separate vessel a 5% sodium hydroxide solution is prepared using 2.5% of the water.

In another vessel the carbomer 980 is gradually combined with the remaining water with agitation to disperse and hydrate the carbomer. The carbomer dispersion is then transferred to a vessel equipped with a high shear mixer (Day Mixer, Serial No. 88612, Day Mixing, Cincinnati, Ohio.) for blending the remaining ingredients. Next, the disodium EDTA is added and mixed until dissolved. The dioctyl sodium sulfosuccinate is then added and stirred until uniform. The bentonite is added to the mixture which is stirred with sufficient agitation until dispersed. Next, the benzoyl peroxide slurry is added and the mixture is stirred until uniform. The dimethicone is then added and the mixture stirred for 5 minutes to fully disperse the silicone. Next, the 5% NaOH solution is gradually added with continuous mixing. The compositions is then mixed for 3–5 minutes until homogeneous.

The resulting anti-acne composition exhibits low skin irritation and good physical and chemical stability, and is useful for topical application to human skin for the treatment of acne.

EXAMPLE 5

Anti-Acne Gel

An antiacne gel is prepared by combining the following ingredients using conventional mixing techniques.

| Ingredients | Weight Percent |
| --- | --- |
| Water | qs100 |
| Benzoyl Peroxide[1] | 2.50 |
| Carbomer 980[2] | 0.65 |
| Disodium EDTA | 0.10 |
| Sodium Hydroxide | 0.12 |
| Bentonite | 1.0 |
| Dimethicone Copolyol[3] | 0.10 |
| Cyclomethicone (and) Dimethiconol[4] | 3.0 |

[1]Lucidol ® 70 from Elf Atochem, which is a powder containing 70% benzoyl peroxide active. 3.57% percent of this powder is added to the composition to account for the 70% activity.
[2]Carbopol ® 980 from B.F. Goodrich.
[3]Dow Corning ® 193 from Dow Corning.
[4]Dow Corning ® Q2-1401 Fluid from Dow Corning.

In a suitable vessel a benzoyl peroxide slurry is prepared by combining the benzoyl peroxide with 17% of the water. This slurry is passed through a Colloid or Urschel mill to disperse the benzoyl peroxide, followed by rinsing the mill with approximately an additional 6% of the water, this rinse being added to the total slurry.

In a separate vessel a 5% sodium hydroxide solution is prepared using 2.5% of the water.

In another vessel the carbomer 980 is gradually combined with the remaining water with agitation to disperse and hydrate the carbomer. The carbomer dispersion is then transferred to a vessel equipped with a high shear mixer (Day Mixer, Serial No. 88612, Day Mixing, Cincinnati, Ohio.) for blending the remaining ingredients. Next, the disodium EDTA is added and mixed until dissolved. The dimethicone copolyol is then added and stirred until uniform. The bentonite is added to the mixture which is stirred with sufficient agitation until dispersed. Next, the benzoyl peroxide slurry is added and the mixture is stirred until uniform. The cyclomethicone (and) dimethiconol is then added and the mixture stirred for 5 minutes to fully disperse the silicone. Next, the 5% NaOH solution is gradually added with continuous mixing. The compositions is then o mixed for 3–5 minutes until homogeneous.

The resulting anti-acne composition exhibits low skin irritation and good physical and chemical stability, and is useful for topical application to human skin for the treatment of acne.

What is claimed is:

1. An anti-acne composition comprising:
   (a) from about 0.1% to about 20% benzoyl peroxide particles,
   (b) from about 0.01% to about 10% of a wetting agent,
   (c) from about 20% to about 99.74% water,
   (d) from about 0.1% to about 10% of a non-volatile emollient component which is a liquid at 25° C. and which has a weighted arithmetic mean solubility parameter of less than or equal to about 7, and
   (e) from about 0.05% to about 5% of a water soluble or dispersible gelling agent.

2. A composition according to claim 1 comprising from about 0.5% to about 15% benzoyl peroxide.

3. A composition according to claim 1 comprising from about 2.5% to about 10% benzoyl peroxide.

4. A composition according to claim 3 wherein said wetting agent is a dimethicone copolyol corresponding to the chemical formula $(CH_3)_3SiO[(CH_3)_2SiO]_x[(CH_3)RSiO]_ySi(CH_3)_3$ wherein R is $C_3H_5O(C_2H_4O)_m(C_3H_6O)_nH$, x is an integer from 1 to about 500, y is an integer from about 1 to about 500, x is an integer from about 1 to about 250, and y is an integer from about 1 to about 250.

5. A composition according to claim 3 wherein said wetting agent is selected from the group consisting of dioctyl sodium sulfosuccinate, sodium lauraminodipropionate, caprylyl pyrollidone, dimethyl octynediol, tetramethyl decynediol, and mixtures thereof.

6. A composition according to claim 3 wherein said wetting agent is dioctyl sodium sulfosuccinate.

7. A composition according to claim 4 wherein said emollient component is selected from the group consisting of silicones, hydrocarbons, esters, and mixtures thereof.

8. A composition according to claim 7 wherein said emollient is a silicone selected from the group consisting of polyalkylsiloxanes, cyclic polyalkylsiloxanes, polyalkylarylsiloxanes, and mixtures thereof.

9. A composition according to claim 8 wherein said emollient is a polyalkylsiloxane corresponding to the chemical formula $R_3SiO[R_2SiO]_xSiR_3$ wherein R is an alkyl group selected from methyl or ethyl and x is an integer from 0 to about 500.

10. A composition according to claim 9 wherein R in said polyalkylsiloxane is methyl.

11. A composition according to claim 8 wherein said emollient is a cyclic polyalkylsiloxane corresponding to the chemical formula $[SiR_2\text{-}O]_n$ wherein R is an alkyl group selected from methyl or ethyl, and n is an integer from about 3 to about 7.

12. A composition according to claim 8 wherein said emollient is a hydrocarbon selected from the group consisting of dodecane, squalane, cholesterol, hydrogenated polyisobutylene, docosane, hexadecane, isohexadecane, paraffins, mineral oil, and mixtures thereof.

13. A composition according to claim 8 wherein said emollient is an ester selected from the group consisting of diisopropyl adipate, isopropyl myristate, isopropyl palmitate, myristyl propionate, ethylene glycol distearate, 2-ethylhexyl palmitate, isodecyl neopentanoate, C12–15 alcohols benzoate, di-2-ethylhexyl maleate, cetyl palmitate, myristyl myristate, stearyl stearate, cetyl stearate, behenyl behenrate, and mixtures thereof.

14. A composition according to claim 9 wherein said water soluble or dispersible gelling agent is selected from the group consisting of carboxylic acid polymers, crosslinked polyacrylate polymers, polacrylamide polymers, polysaccharides, gums, crosslinked ether/maleic anhydride copolymers, cellulosic thickeners, crosslinked poly(N-vinylpyrrolidones), and mixtures thereof.

15. A composition according to claim 14 wherein said gelling agent is a carboxylic acid polymer selected from the group consisting of carbomers, acrylates/C 10–30 alkyl acrylate cross polymers, and mixtures thereof.

16. A composition according to claim 15 wherein said benzoyl peroxide has an average particle size diameter from about 0.5 to about 40 microns.

17. A method for the treatment of acne in a human in need thereof comprising the topical application of an anti-acne effective amount of the composition of claim 1.

18. A method for the treatment of acne in a human in need thereof comprising the topical application of an anti-acne effective amount of the composition of claim 4.

19. A method for the treatment of acne in a human in need thereof comprising the topical application of an anti-acne effective amount of the composition of claim 7.

20. A method for the treatment of acne in a human in need thereof comprising the topical application of an anti-acne effective amount of the composition of claim 15.

* * * * *

UNITED STATES PATENT AND TRADEMARK OFFICE
CERTIFICATE OF CORRECTION

PATENT NO. : 5,470,884     Page 1 of 2

DATED : November 28, 1995

INVENTOR(S) : Ann Marie Corless et al.

It is certified that error appears in the above-identified patent and that said Letters Patent is hereby corrected as shown below:

At column 2, line 28 "anti-ache" should read --anti-acne--.

At column 6, line 30 "the s Vicasil" should read --the Vicasil--.

At column 7, line 10 "Herein" should read --herein--.

At column 7, line 21 "cholesterol, 5" should read --cholesterol,--.

At column 8, line 10 "alkyl —CN —COOH and" should read --alkyl, —CN, —COOH, and--.

At column 9, line 9 "C 10-C30" should read --C10-C30--.

At column 9, line 30 "$(A)_l$," should read --$(A)_r$--.

At column 9, line 31 "$(A)_l$," should read --$(A)_r$--.

At column 9, line 50 "$C_1-C^2$" should read --$C_1-C_2$--.

At column 9, lines 51-52 "alkyls i.e. " should read --alkyls, i.e.,--.

At column 9, line 52 "preferably $C_1-C_8$" should read --preferably $C_1-C_5$--.

At column 9, line 57 "$(A)_l$," should read --$(A)_r$--.

At column 9, line 58 "typically material" should read --typically a material--.

At column 11, line 1 "to o about" should read --to about--.

At column 11, line 16 "$(A)_l$," should read --$(A)_r$--.

At column 11, line 16 "I is zero" should read --l is zero--.

At column 11, line 31 "I is also zero" should read --l is also zero--.

At column 11, line 38 "$(A)_l$," should read --$(A)_r$--.

At column 11, line 38 "I is zero" should read --l is zero--.

At column 12, lines 2-3 "laureth7" should read --laureth-7--.

UNITED STATES PATENT AND TRADEMARK OFFICE
CERTIFICATE OF CORRECTION

PATENT NO.    :    5,470,884

DATED    :    November 28, 1995

INVENTOR(S)    :    Ann Marie Corless et al.

It is certified that error appears in the above-identified patent and that said Letters Patent is hereby corrected as shown below:

At column 12, line 29 "C  10-C30" should read --C10-C30--.

At column 12, line 53 "guar lo hydroxypropyltrimonium" should read --guar hydroxypropyltrimonium--.

At column 13, line 2 "$C_l$–C6" should read --C1–C6--.

At column 13, line 36 "ACP1180" should read --ACP-1180--.

At column 14, line 62 "Lucidol ® 700" should read --Lucidol® 70--.

At column 15, line 47 "14,29%" should read --14.29%--.

At column 17, line 6 "Perxodie¹" should read --Peroxide¹--.

At column 18, line 30 "then o mixed" should read --then mixed--.

At column 20, line 12 "C  10-30" should read --C10-30--.

Signed and Sealed this

Ninth Day of March, 1999

Attest:

Q. TODD DICKINSON

*Attesting Officer*    *Acting Commissioner of Patents and Trademarks*

(12) EX PARTE REEXAMINATION CERTIFICATE (8406th)
United States Patent
Corless et al.

(10) Number: US 5,470,884 C1
(45) Certificate Issued: Jul. 19, 2011

(54) ANTI-ACNE COMPOSITIONS

(75) Inventors: Ann M. Corless, Fairfield, OH (US); George E. Deckner, Cincinnati, OH (US); Bonnie J. Hall, Mason, OH (US); Joseph A. Listro, Loveland, OH (US)

(73) Assignee: Reckitt & Colman (Overseas) Limited, Slough, Berkshire (GB)

Reexamination Request:
No. 90/010,935, May 10, 2010

Reexamination Certificate for:
Patent No.: 5,470,884
Issued: Nov. 28, 1995
Appl. No.: 08/245,777
Filed: May 19, 1994

Certificate of Correction issued Mar. 9, 1999.

(51) Int. Cl.
| | |
|---|---|
| A61K 8/38 | (2006.01) |
| A61K 8/894 | (2006.01) |
| A61K 31/00 | (2006.01) |
| A61K 31/327 | (2006.01) |
| A61K 33/40 | (2006.01) |
| A61K 47/34 | (2006.01) |
| A61P 17/10 | (2006.01) |
| A61Q 19/00 | (2006.01) |

(52) U.S. Cl. .................................. 514/714; 514/864
(58) Field of Classification Search .................. None
See application file for complete search history.

(56) References Cited

U.S. PATENT DOCUMENTS

| 4,478,853 A | 10/1984 | Chaussee |
| 4,692,329 A | 9/1987 | Klein et al. |
| 4,917,891 A | 4/1990 | Kaufmann et al. |
| 5,073,371 A | 12/1991 | Turner et al. |
| 5,145,685 A | 9/1992 | Carmody |
| 5,204,093 A | 4/1993 | Victor |
| 5,470,551 A | 11/1995 | Dubief et al. |

*Primary Examiner* — Gary L Kunz

(57) ABSTRACT

The present invention relates to anti-acne compositions having good efficacy, low skin irritation, and good physical and chemical stability. These compositions comprise a benzoyl peroxide, a wetting agent, water, a non-volatile emollient component which is a liquid at 25° C. and which has a weighted arithmetic mean solubility parameter of less than or equal to about 7, and a water soluble or dispersible gelling agent.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4, 12 and 13 are determined to be patentable as amended.

Claims 2, 3, 5-11 and 14-20, dependent on an amended claim, are determined to be patentable.

1. An anti-acne composition comprising:
   (a) from about 0.1% to about 20% benzoyl peroxide particles,
   (b) from about 0.01% to about 10% of a wetting agent,
   (c) from about 20% to about 99.74% water,
   (d) from about 0.1% to about 10% of a non-volatile emollient component which is a liquid at 25° C. and which has a weighted arithmetic mean solubility parameter of less than or equal to [about] 7, and
   (e) from about 0.05% to about 5% of a water soluble or dispersible gelling agent.

4. A composition according to claim 3 wherein said wetting agent is a dimethicone copolyol corresponding to the chemical formula $(CH_3)_3SiO[(CH_3)_2SiO]_x[(CH_3)RSiO]_ySi(CH_3)_3$ wherein R is $C_3H_5O(C_2H_4O)_m(C_3H_6O)_nH$, x is an integer from 1 to about 500, y is an integer from about 1 to about 500, [x] *m* is an integer from about 1 to about 250, and [y] *n* is an integer from about 1 to about 250.

12. A composition according to claim [8] *7* wherein said emollient is a hydrocarbon selected from the group consisting of dodecane, squalane, cholesterol, hydrogenated polyisobutylene, docosane, hexadecane, isohexadecane, paraffins, mineral oil, and mixtures therof.

13. A composition according to claim [8] *7* wherein said emollient is an ester selected from the group consisting of diisoproplyl adipate, isopropyl myristate, isopropyl palmitate, myristyl propionate, ethylene glycol distearate, 2-ethylhexyl palmitate, isodecyl neopentanoate, C12-15 alcohols benzoate, di-2-ethylhexyl maleate, cetyl palmitate, myristyl myristate, stearyl stearate, cetyl stearate, behenyl behenrate, and mixtures thereof.

* * * * *